United States Patent [19]
Filler et al.

[11] Patent Number: 6,153,598
[45] Date of Patent: Nov. 28, 2000

[54] SYNTHETIC TRANSFECTION VECTORS

[75] Inventors: Aaron Gershon Filler, Seattle, Wash.;
Andrew Michael Lindsay Lever,
Cambridge, United Kingdom

[73] Assignee: Syngenix Limited, United Kingdom

[21] Appl. No.: 09/062,145

[22] Filed: Apr. 17, 1998

Related U.S. Application Data

[62] Continuation of application No. 08/583,195, Jan. 4, 1996, abandoned, which is a continuation of application No. 08/211,041, filed as application No. PCT/GB92/01703, Jun. 16, 1992, abandoned.

[51] Int. Cl.[7] .............................. A61K 48/00; A61K 9/16
[52] U.S. Cl. ........................... 514/44; 424/490; 424/491; 424/493
[58] Field of Search ................ 514/44; 424/490, 424/491, 493

[56] References Cited

U.S. PATENT DOCUMENTS 4,452,773  6/1984  Molday ................................. 424/1.1

FOREIGN PATENT DOCUMENTS

| | | |
|---|---|---|
| 0040512 | 11/1981 | European Pat. Off. . |
| 2221466 | 2/1990 | United Kingdom . |
| 8807365 | 10/1988 | WIPO . |
| 8903675 | 5/1989 | WIPO . |
| 9204916 | 4/1992 | WIPO . |
| 9205250 | 4/1992 | WIPO . |
| 9211037 | 7/1992 | WIPO . |
| 9211846 | 7/1992 | WIPO . |

OTHER PUBLICATIONS

Cotten, M. et al. (1992) High–efficiency receptor–mediated delivery of small and large 48 kilobase gene constructs using the endosome–disruption activity of defective or chemically inactivated adenovirus particles. Proc. Natl. Acad. Sci. USA 89: 6094–6098.

Audesirk, G., Audesirk, T. (1986) Biology: Life on Earth. New York, MacMillan Publishing Company, pp. 66–67.

Wu, G.Y., Wu, C.H. (1988) Receptor–mediated Gene Delivery and Expression in Vivo. The Journal of Biological Chemistry 263(29): 14621–14624.

Walker, P.R. et al. (1989) Effects of Aluminum and Other Cations on the Structure of Brain and Liver Chromatin. Biochemistry 28: 3911–3915.

*Primary Examiner*—Bruce R. Campell
*Attorney, Agent, or Firm*—Saliwanchik, Lloyd & Saliwanchik

[57] ABSTRACT

An inorganic particle, to which is bonded a cell binding component and a nucleic acid, is provided for delivery of a nucleic acid to a cell. The disclosed particle acts as a synthetic vector for achieving efficient transfection of associated nucleic acid into a cell.

4 Claims, No Drawings

SYNTHETIC TRANSFECTION VECTORS

CROSS-REFERENCE TO RELATED APPLICATIONS

This application is a continuation of application Ser. No. 08/583,195, filed Jan. 4, 1996 abandoned; which is a file wrapper continuation of application Ser. No. 08/211,041, filed Sep. 16, 1992, now abandoned which was a national stage application of PCT/GB92/01703, filed Jun. 16, 1992.

FIELD OF THE INVENTION

This invention relates to synthetic transfection vectors.

This invention is in the field of gene therapy and concerns the design and use of an entirely novel means of safely introducing therapeutic genes into mammalian and human cells to achieve various useful effects.

Steady progress over the past twenty years in the field of genetic engineering, nucleic acids research, chromosome mapping, DNA cloning, and other related fields has brought modern medicine to the threshold of gene therapy. It may be possible to treat some diseases by constructing pieces of DNA or RNA which code information which could correct the physiological malfunction causing the disease. It may also be possible in agriculture to make certain beneficial changes in the protein product of some animals or plants.

A crucial limiting factor in progress in this field is the difficulty of causing such new genes to enter the cells of intact organisms where they can commence doing their work. For some small animals and plants, genes have been introduced into the small number of cells involved in the early embryo and so caused to replicate and ultimately appear in many or all of the cells of the adult organism. However, this approach is not viable for treating diseases in human children or adults where the disease is discovered after conception or more commonly after birth. Further, in agriculture, this method proves to be extremely expensive and difficult to carry out when large numbers of large animals such as cattle are meant to be so treated.

A variety of methods have been attempted for introducing genes into adult animals. These methods include direct injection of naked DNA plasmids into individual cells, attempts at reapplying calcium phosphate transfection techniques, inclusion of DNA into liposomes, and construction of simulated viruses which can carry the new DNA as a sort of infection. The greatest progress has been made with a group of techniques in which DNA is coated onto gold colloid particles and the particles then subject to powerful electromagnetic fields in order to accelerate them to high speeds and so to hurl them against the cell walls of tissues. The particles plunge through the tissue surface and many viable DNA chains arrive inside the cell along with their non-degradable gold carrier. To reach tissues other than skin, a surgical operation is performed, and e.g. the tip of the liver is exposed and then a bombardment is carried out. This permits access only to surface layers of exposed tissues, is obviously injurious (since petechial haemorrhages immediately appear on the tissue surface), and deposits substantial amounts of non-degradable gold in the tissues.

BRIEF SUMMARY OF THE INVENTION

In the method of this invention, the new DNA, RNA, plasmids, ribosomal particles, nucleic acid binding proteins and any other necessary molecules are caused to adhere to the outer surface of any one of a variety of metal oxide or mixed metal crystals of coated or uncoated type or to be attached to the surface of or included in the body of a variety of other types of biodegradable particles of appropriate size and capable of surface attachment to a cell adhesion molecule. These particles are in the size range of 5 to 100 nm in diameter including all attached coatings and other surface molecules. Included on the surface is one of a variety of nerve adhesion molecules or muscle adhesion molecules which bind to the surface of nerve and muscle cells, but preferably to muscle cells.

When such particles are constructed and then administered by routine percutaneous intramuscular injection, an exceedingly safe and efficient transfection process is initiated. The particles adhere to the outer surfaces of muscle cells and to the outer surfaces of the axon termini of motor nerve cells or preferably to the dendritic or sensory process of sensory axons within the muscle. After adherence, the particles are ingested into the nerve and muscle cells by a natural process termed adsorptive endocytosis.

DETAILED DESCRIPTION OF THE INVENTION

Experiments carried out by the inventor have demonstrated a surprising efficiency for the uptake of such particles after intramuscular injection. Further, particularly when such particles are made of iron salts, the particles are completely biodegradable. Normally, particulate material injected into muscle is rapidly cleared by the lymphatic system and the particles are taken into lysosomal vesicles where they are subject immediately to degradative enzymes. However, the inventor has shown that when the process of adsorptive endocytosis by muscle cells is entrained, the bulk of the injected material is carried into protected compartments within neural and muscular cells.

Many cells have means of destroying any foreign DNA or RNA which appears in their cytoplasmic compartments, however muscle cells are uniquely ineffective at destroying incoming nucleic acids. In this fashion, and using intramuscular injection, the agents can be caused to enter the very large intracellular volume provided by the cells of muscles. Upon uptake by neurons, it is also possible to take advantage of the natural ability of the dendritic processes of neurons to carry out protein synthesis from RNA at great distance from the controlling influence of the neuron cell body. Use of sensory specific nerve adhesion molecules such as Nerve Growth Factor is helpful at efficiently selecting sensory rather than motor neurons where this is useful. In some situations, it may be useful to inject the agent into or near and dorsal root ganglion so that the agent can be carried by axonal transport to reach all of the tissues innervated by sensory processes from cells in that ganglion.

Treatment of muscle cells or treatments where gene therapy products are dumped into the neuromuscular synapse after production in the nerve process terminus are particularly helpful for treating disorders such as muscular dystrophy or other diseases which particularly affect muscle or for treating diseases which affect neuromuscular transmission.

It must be noted, however, that such agents are sufficiently small that they can be safely injected intravenously. Because of their potentially hydrophilic coatings with e.g. dextran, the inventor has shown extended plasma half life for such agents with up to 25% of the initial injectate remaining in circulation for over four hours. This provides targeting access to a wide variety of cells in the blood marrow, circulating blood, and various glands and tissues. In all these cases, selection of appropriate targeting molecules for these particles will cause preferential adsorption to various useful cell types. While efficiency of phagocytosis of selectively adsorbed particles varies among tissues, there are a very wide variety of accessible intracellular sites. When the metal oxide core is constructed in such a way as to demonstrate superparamagnetism, then external magnetic fields (as from U.S. Pat. No. 4,869,247) can be used to aid in targeting the agents.

In one example of synthesis of such compounds, the nucleic acid attachment to the particle is effected by specific nucleic acid binding proteins. A DNA plasmid or strand is constructed to include both the desired treatment gene and a segment with very high affinity for a selected nucleic acid binding protein. This pairing can be optimised by binding the attachment DNA segment to immobile latex particles using a cyanogen bromide immobilisation technique. Various nucleic acid binding proteins and other cell constituents are then passed through an affinity column made up to such DNA tagged latex particles. The specific fraction of nucleic acid binding protein is then eluted for use in making the particle.

A mixture of ferrous and ferric chloride salts is dissolved in a saturated dextran solution after the fashion of U.S. Pat. No. 4,452,773 and precipitated by addition of 7.5% ammonia solution. The product is then moved into 0.1 M acetate buffer pH 6.4 by Sephadex 150 column filtration, concentrated with Amicon Centriprep 30 ultrafilters, and passed through a 2.5 cm by 20 cm column of Sephacryl 200 to clear gelatinous hydrous oxides and excess dextran.

The particles are then filtered at 200 nm and 100 nm and next gently oxidised in 20 mM $NaIO_4$. The $NaIO_4$ is cleared with PD-10 sephadex columns and the same column used to transfer the particles into a pH 8.0 borate buffer solution. The nerve adhesion molecule such as wheat germ agglutinin or transferrin or nerve growth factor with appropriate blocking of active sites (Ca and Mn chlorides) and the appropriate nucleic acid binding protein with small nucleic acid fragments to block the active site are then incubated with the particles for 8 to 12 hours. After this, remaining active sites are blocked by adding 1 M glycine for 2 additional hours, and the mixture then reduced with $NaBH_4$ for one hour. After reducing the covalent bonds, the particles are moved into HEPES 20 mM pH 7.4 buffer through PD-10 columns which also serve to clear unreacted glycine, $NaBH_4$, and any dissolved iron salts. The product is diluted in HEPES buffer, then reconcentrated with Amicon Centriprep 100 ultrafilters to help clear unbound proteins, and then passed through Sephacryl 200 or other Sephacryl size column to clear additional unreacted protein.

The output from these columns is then reconcentrated with Amicon Centriprep-100 ultrafilters and subject to two rounds of affinity purification. The first round is on a column carrying the muscle surface or neural surface or other desired cell surface marker. In this fashion, all particles which will not adhere to the desired target cells are eliminated. The affinity fraction is eluted, diluted, reconcentrated, and the subjected to a second affinity purification but this time against a column with immobilised DNA fragments which are recognised by the nucleic acid binding protein now ligated to the particle surface.

The highly purified product of the second affinity step is now diluted in HEPES 20 mM pH 7.4, reconcentrated with Amicon Centriprep-100 or similar ultrafilters and then exposed to the genetic material to be delivered. When a mixed plasmid or strand is used, the binding protein interacts with the binding portion of the DNA and the large nucleic acid molecule carries with it the active gene of interest. It is also possible to use nucleic acid binding proteins which bind directly to a gene or segment of RNA or DNA of interest when such binding proteins are available.

The particles with bound DNA are passed through a Sephacryl column to clear unbound nucleic acid if desired and are now ready for concentration and dilution in an appropriate physiological solution for intramuscular injection. The agent is now injected into muscle whereupon natural processes of adhesion and endocytosis complete the gene transfection into the selected cell type.

In another example of the preparation, the initial precipitation of the iron salts is done by dropwise addition to ammonia solution without the presence of any coating dextran or other molecule. The resulting suspension is spun in a centrifuge at 500 g for 10 minutes and the pellet washed and resuspended in distilled water and the process then repeated but with a wash with 0.01N HCl. The resulting stable colloid is then exposed to a mixture of adhesion molecule protein, nucleic acid strands and/or nucleic acid binding proteins. After an incubation with gentle nonmagnetic stirring for one hour, the remaining reactive sites on the particles are blocked by the addition of dextran or albumin protein. The particles are then passed through sephadex 150 and Sephacryl 200 columns then affinity purified by means of the cell adhesion molecule using for instance a column of affinity labelled agarose, sepharose, or latex beads.

In yet another example of the preparation, the initial precipitation is carried out by preparing a solution of very strong buffer such as 1 Molar or higher concentration of HEPES or Tris at a pH of 7.4. The nucleic acids, any desired dextran, and or targeting proteins and nucleic acid binding proteins are added directly to this initial strong buffer. The mixture of dissolved ferrous and ferric iron salts in aqueous solution or in a solution containing dextran and/or protein and/or nucleic acids is then added dropwise to the buffer solution. In this fashion, the particles are formed in a rigidly buffered solution and so many fragile protein and peptide molecules can be used to form the particle coat where such molecules are Necessary for targeting, for introducing ribonucleoprotein or ribosomal protein or other aspects of transcription signalling or actual transcription mechanism proteins along with the DNA or RNA. The product of this precipitation reaction is then further blocked with dextran or albumin if necessary, then purified with sephadex 150, sephacryl 200, Amicon ultrafilters and affinity columns as described above.

In yet another version of the synthesis, there is no nucleic acid binding protein used but only a cell surface adhesion molecule. Instead of the nucleic acid binding protein, a complementary fragment of the nucleic acid of interest is bound to the particles by a cyanogen bromide or other type of binding reaction or by adherence to an uncoated particle type. The gene of interest is then attached to the particle by its interaction with the bound complementary fragment after which purification steps are carried out as described above.

In summary, the present invention provides a synthetic transfection agent, the corresponding vector without the nucleic acid, and any combination of the components thereof. It will be appreciated that the synthetic transfection agent is based on precipitation of one of a variety of ceramic metal oxide particles similar in size to a virus. The metal oxide particle is coated with dextran or other biologically-tolerable polymer during the precipitation process. Chemically, the basic structure is similar to drugs in current use as magnetic resonance contrast agents.

The dextran or other coating of the particle is used as a framework to which various other types of molecules are then covalently bound. Typically, a targeting molecule such as an antibody or antibody fragment, or some other useful cell adhesion molecule is used. This causes the particle to adhere selectively to certain desirable cell types, e.g. a gp120 fragment to promote adherence to CD4 positive cells. In addition to the targeting molecule, it is also possible to attach a nucleic acid binding protein or short cDNA sequence to the dextran coat. In this fashion, particles can be produced with appropriate nucleic acid binding proteins and targeting molecules, and then subsequently loaded with the therapeutic DNA.

For intravascular administration, the particle size determines serum half-life and destination. Larger particles tend to be cleared into the reticuloendothelial cells by phagocytosis, while small particles achieve destinations determined more completely by their targeting molecule.

These particles can also be administered intramuscularly where they can gain entry into muscle cells and also can be ingested by nerve terminals in the muscle and subsequently subjected to axonal transport from the periphery towards the neural cell bodies in the central nervous system. In this fashion, mimicking the route of the Herpes virus, an intramuscular injection can be used to deliver DNA across the blood-brain barrier for therapeutic purposes in selected regions of the nervous system. The axonal transport route also provides access to Schwann cells which line the axons.

It is further possible to provide the particles in aerosol form for pulmonary administration. A variety of other routes of administration are also feasible, including intravenous administration.

The particulate carrier is well suited for treating diseases involving the reticuloendothelial system through intravascular and inhalational routes, and to treat GI mucosal cells by enteral routes, as well as for intramuscular injection for access to muscle cells. Access via the intraneural route, to CNS and ganglion cells, is provided by intramuscular and intradermal injection.

It has been demonstrated that the particles are ingested by human macrophages, T-cells and osteogentic sarcoma cells, and that there is slow clearance of the particles from the blood stream in a rabbit, with 25% of the injected dose remaining in the circulation after four hours. Particles have coated with dextran and conjugated to both anti-CD4 and DNA polymerase as a nucleic acid-binding protein, with subsequent exposure to and uptake of DNA plasmids onto the particle surface. Particles may also be coated with DNA directly, rather than with dextran.

The particles are biodegradable in the sense that they can break down, in vivo, to materials that are essentially harmless. Thus, for example, while foreign materials such as gold particles may be found intact in cells years later, iron oxide particles dissolve readily into oxygen and iron, both of which are of course naturally present in abundance in cells and which then participate in normal cellular metabolism, storage and reuse. Iron poses some risk of toxicity when present in high amounts. The potential toxicity of ferrites is reduced by ensuring that they dissolve slowly, at a rate no faster than the cells' ability to process the elemental iron. Extension of the degradation rate for the particles can be achieved by ensuring that the original preparation is free of hydrous oxides of iron that are similar in overall size and chemical composition to ferrites but dissolve very rapidly. Additionally, by doping in other elements such as palladium (which is water-soluble in elemental form unlike gold) which can improve the stability of the ferrite, the rate of breakdown can be slowed.

The ceramic particle-based system disclosed here has advantages over viral vectors, in that there is no risk of infection or of introduction of unwanted viral genes. It has advantages over the gold colloid system in that the particles are biodegradable. Further, since they may have a coat to which proteins may be covalently bound, these particles can be injected into the body via less drastic and more traditional pharmaceutical routes. The facility with which various proteins and enzymes can be bound to the particle surface makes them far more flexible and complex as delivery agents than simple lipid spheres.

Because of the size of the particles as used in this invention, they can be filter-sterilised and subjected to affinity chromatography before DNA is loaded. This means that particle carriers can be sold independent of the DNA and can serve as a convenient synthetic vector for a wide variety of applications. It is also convenient to label the metal oxide core with radioactive emitters where this is useful to trace their distribution.

The preparation of inorganic, metal oxide particles for therapeutic delivery is described in WO-A-9204916. In the illustrative Example that follows, the preparation of the particles gives desirable homogeneity and avoidance of water-soluble materials that may adversely affect the desired slow metabolism. The Example obviates column chromatography, for which the use of centrifugal concentrators has been substituted, and involves the corresponding omission of NaCl elution buffers. EDTA is used as a chelating agent in the buffer used in the first washing steps. This apparently dissolves the iron in the hydrous oxides, but does not dissolve the well-formed ferrites. The result is a stable and uniform particle preparation with low toxicity (because it is a substantially pure ceramic preparation).

EXAMPLE

Use double distilled water (not de-ionised) to make up the reaction mixture. The following steps are conducted:

Add 1.5 ml of 33% $NH_3$ to 4.5 ml of hot $dH_2O$ (to make up 7.5% $NH_4OH$) and leave standing in a capped universal tube in the water bath and bring to 60° C.

Dissolve 1.25 g Dextran (MW 10,000) in 2.0 ml of $ddH_2O$ then dissolve 225 mg $FeCl_3.6H_2O$ in the dextran solution. Alternatively, a trivalent lanthanide chloride may be substituted for 10 to 50% of the $FeCl_3$. When this is done, the subsequent post-reaction incubation is extended to two hours.

Dissolve 100 mg $FeCl_2.4H_2O$ in the $Fe_3$/dextran solution then place the mixture in a 60° C. water bath for two minutes before starting to gradually add 6 ml of hot 7.5% $NH_3$ solution (60° C.). The product is left to stand in the 60° C. water bath for fifteen minutes.

The reaction product (dextran-coated ferrites) is spun at 1,000 g for 10 minutes and any precipitate is discarded. This process is repeated to complete three spins and the supernatant then applied to PD-10 columns equilibrated with 0.1 M NaAcetate buffer, pH 6.8 with 5 mM EDTA.

The black eluted fraction is diluted 1:3 with EDTA/Acetate buffer then concentrated to one-tenth the initial volume with Amicon Centriprep-100 ultrafilters. The retentate is then diluted 1:10 with EDTA/Acetate buffer then concentrated to a volume of 1.5 ml with the C-100 ultrafilters.

Add 0.30 ml of 20 mM $NaIO_4$ to the dextran ferrite solution (approx. 1.5 ml) while stirring then gently tumble or shake for 60 minutes at room temperature in the dark.

At the end of the 60-minute periodate incubation, the reaction is terminated by applying the reaction mixture to the PD-10 columns equilibrated with 20 mM borate buffer (pH 8.5).

An active site blocking solution is prepared using 100 mM $MnCl_2/CaCl_2$ for WGA binding reactions. Alternatively, e.g. calf thymus DNA can be used where the protein active site to be protected is on a nucleic acid binding protein.

Dissolve 10 mg of the protein (e.g. DNAse free DNA pol 1, Klenow fragment, integrase, useful proteins for subsequent translation steps, nucleic acid packaging protein and anti-CD4, WGA, or other cell-targeting protein) in 500 μl of 20 mM Na borate buffer, pH 8.5 at room temperature. The protein solution can be diluted to 12 ml with borate buffer, then concentrated with Centriprep-10 concentrators to remove DTT, glycerol, $NaN_3$ and other undesirable storage additives.

Add 10 μl of the blocking solution to the protein/borate solution then mix 2.0 ml of oxidised magnetite dextran with 500 μl of the protein/borate solution. Pipette 20 μl of the blocking solution into the 2.5 ml protein-dextran-magnetite mixture and mix well, then incubate for 6 to 18 hours at room temperature in a gentle tumbling or shaking device.

After the incubation, add 100 μl of 0.5 M glycine to the reaction mixture and incubate an additional 2 hours. Then add 250 μl of 0.25 M $NaBH_4$ to the magnetite-dextran-protein solution and allow to stand for 60 minutes, shaking periodically to release $H_2$ gas. At the end of the incubation, pass the reaction mixture through PD-10 columns equilibrated with 20 mM HEPES buffer, pH 7.4. Dilute the eluant 1:5 with HEPES buffer then concentrate with Centriprep-100 ultrafilters.

An affinity purification step is optional and detail is given for use with a WGA(lectin) targeting protein. Apply final retentate to affinity columns (20 mM HEPES), wash with HEPES, then carry out specific elution with 1 M NAcGlu in HEPES buffer, pH 7.4. Pass the specific eluant through PD-10 columns equilibrated with HEPES to remove NAcGlu, Mn and Ca.

The desalted output is then diluted to a volume of 24 ml with HEPES buffer and concentrated with Centriprep-100 concentrators. The final retentate is sterilised by spinning at 500 h for one hour in 0.22 μm centrifugal microfilters.

The purified, sterilised synthetic vector particles can now be stored at 4° C. for use within one to two weeks. They should not be frozen or lyophilised.

DNA adhesion with the DNA of interest can be done immediately prior to the transfection. The particle solutions are incubated with the DNA of interest with gentle tumbling or shaking for 6 to 24 hours.

Depending on the experimental or therapeutic protocol, the DNA-loaded vector solution may then be applied to cell cultures at a concentration of 1 mg/ml (approx. 5 mM Fe) of the synthetic vector (the final product of the preparation is 25 to 50 mg of synthetic vector). To assess efficiency, it may be compared to unadsorbed DNA solution. Alternatively, the DNA-loaded synthetic vector may be administered by IV or IM routes for in vivo use at 10 to 100 mM concentration. Non-precipitating magnetic-based separation techniques can be used to separate unbound DNA from particles. Where smaller DNA molecules are used, the separation can be done with Centriprep-100 concentrators.

What is claimed is:

1. Ferrite particles which are free of hydrous oxides chelatable with EDTA, wherein said particles are coated with a biologically-tolerable polymer.

2. The ferrite particles according to claim 1, wherein said particles carry DNA, RNA, plasmids, ribosomal particle s or nucleic acid-binding proteins.

3. The ferrite particles according to claim 1, wherein said particles carry a nerve adhesion molecule.

4. The ferrite particles according to claim 1, wherein said biologically-tolerable polymer is dextran.

* * * * *

UNITED STATES PATENT AND TRADEMARK OFFICE
CERTIFICATE OF CORRECTION

PATENT NO. : 6,153,598
DATED : November 28, 2000
INVENTOR(S) : Aaron Gershon Filler, Andrew Michael Lindsay Lever It is certified that error appears in the above-identified patent and that said Letters Patent is hereby corrected as shown below:

Title page,
Item [62] Related U.S. Application Data,
"Continuation of application No. 08/583,195, Jan. 4, 1996, abandoned,
which is a continuation of application No. 08/211,041, filed as application
No. PCT/GB92/01703, Jun. 16, 1992, abandoned."
should read
-- Continuation of application No. 08/583,195, Jan. 4, 1996, abandoned,
which is a continuation of application No. 08/211,041, March 16, 1994, abandoned,
filed as application No. PCT/GB92/01703, Sept. 16, 1992. --.

Column 1,
Line 9, "Sep. 16, 1992" should read -- March 16, 1994 --.
Line 10, "Jun. 16, 1992" should read -- Sept. 16, 1992 --.

Signed and Sealed this

Twenty-sixth Day of February, 2002

Attest:

JAMES E. ROGAN
*Attesting Officer*  *Director of the United States Patent and Trademark Office*